United States Patent
Robinson

(10) Patent No.: US 6,790,192 B2
(45) Date of Patent: Sep. 14, 2004

(54) HAND AND WRIST BRACE AND KIT

(75) Inventor: Paul K. Robinson, Duck, NC (US)

(73) Assignee: Medical Products Marketing, Inc., Richmond, VA (US)

( * ) Notice: Subject to any disclaimer, the term of this patent is extended or adjusted under 35 U.S.C. 154(b) by 11 days.

(21) Appl. No.: 10/307,660

(22) Filed: Dec. 2, 2002

(65) Prior Publication Data

US 2004/0106889 A1 Jun. 3, 2004

(51) Int. Cl.[7] ............................................. A61F 5/00
(52) U.S. Cl. ........................... 602/21; 602/5; 602/20; 602/22
(58) Field of Search ................... 602/21, 22, 5, 602/20, 62, 64, 75; 128/878, 879

(56) References Cited

U.S. PATENT DOCUMENTS

| | | | | |
|---|---|---|---|---|
| 3,327,703 A | | 6/1967 | Gamm | |
| 4,384,571 A | * | 5/1983 | Nuzzo et al. ................. | 602/22 |
| 4,522,197 A | | 6/1985 | Hasegawa | |
| 4,584,993 A | * | 4/1986 | Nelson ......................... | 602/21 |
| 4,854,309 A | * | 8/1989 | Elsey ........................... | 602/21 |
| 5,000,176 A | | 3/1991 | Daniel | |
| 5,014,689 A | * | 5/1991 | Meunchen et al. .......... | 602/21 |
| 5,415,624 A | | 5/1995 | Williams | |
| 5,513,657 A | * | 5/1996 | Nelson ......................... | 128/879 |
| 5,538,501 A | * | 7/1996 | Caswell ....................... | 602/64 |
| 5,540,735 A | * | 7/1996 | Wingrove ..................... | 607/46 |
| 5,713,837 A | * | 2/1998 | Grim et al. ................... | 602/6 |
| 5,746,707 A | * | 5/1998 | Eck .............................. | 602/21 |
| 5,807,293 A | * | 9/1998 | Wedge, Jr. .................... | 602/21 |
| 5,814,002 A | * | 9/1998 | Nelson ......................... | 602/27 |
| 5,827,207 A | | 10/1998 | MacMorran | |
| 5,836,902 A | | 11/1998 | Gray | |
| 5,921,945 A | | 7/1999 | Gray | |
| 5,976,058 A | | 11/1999 | Gustafson | |
| 6,006,751 A | | 12/1999 | Spitzer | |
| 6,024,715 A | * | 2/2000 | Maxwell ...................... | 602/64 |
| 6,095,994 A | | 8/2000 | Spits | |
| 6,120,471 A | | 9/2000 | Varn | |
| 6,142,966 A | * | 11/2000 | Hely ............................ | 602/64 |
| 6,146,347 A | | 11/2000 | Porrata | |
| 6,155,263 A | * | 12/2000 | Weaver ....................... | 128/878 |
| 6,196,985 B1 | * | 3/2001 | Slautterback ................ | 602/20 |
| 6,199,211 B1 | | 3/2001 | Franzolino | |
| 6,293,918 B1 | | 9/2001 | Wang | |
| 6,293,919 B1 | | 9/2001 | Manente | |
| 6,328,706 B1 | | 12/2001 | Yattavong | |
| 6,383,157 B1 | * | 5/2002 | Massi et al. .................. | 602/21 |
| 6,398,748 B1 | | 6/2002 | Wilson | |
| 6,561,994 B1 | * | 5/2003 | Mills et al. .................... | 602/20 |
| 2002/0035342 A1 | | 3/2002 | Williams | |
| 2002/0040201 A1 | | 4/2002 | Herzberg | |

FOREIGN PATENT DOCUMENTS

DE          3910318 A1       10/1990

* cited by examiner

Primary Examiner—Henry Bennett
Assistant Examiner—Amanda Flynn
(74) Attorney, Agent, or Firm—John H. Thomas, P.C.

(57) ABSTRACT

A brace is adapted to be wrapped around the wrist and hand of a patient. The brace includes a flexible sheet that comprises a central palmar section, a first flap section connected to and disposed on one side of the palmar section, and second flap section connected to and disposed on the opposite side of the palmar section from the first flap. Fasteners are attached to each of the first and second flap sections. Written indicia are printed onto one of the first or second flap sections, wherein the written indicia correspond to predetermined brace sizes.

11 Claims, 9 Drawing Sheets

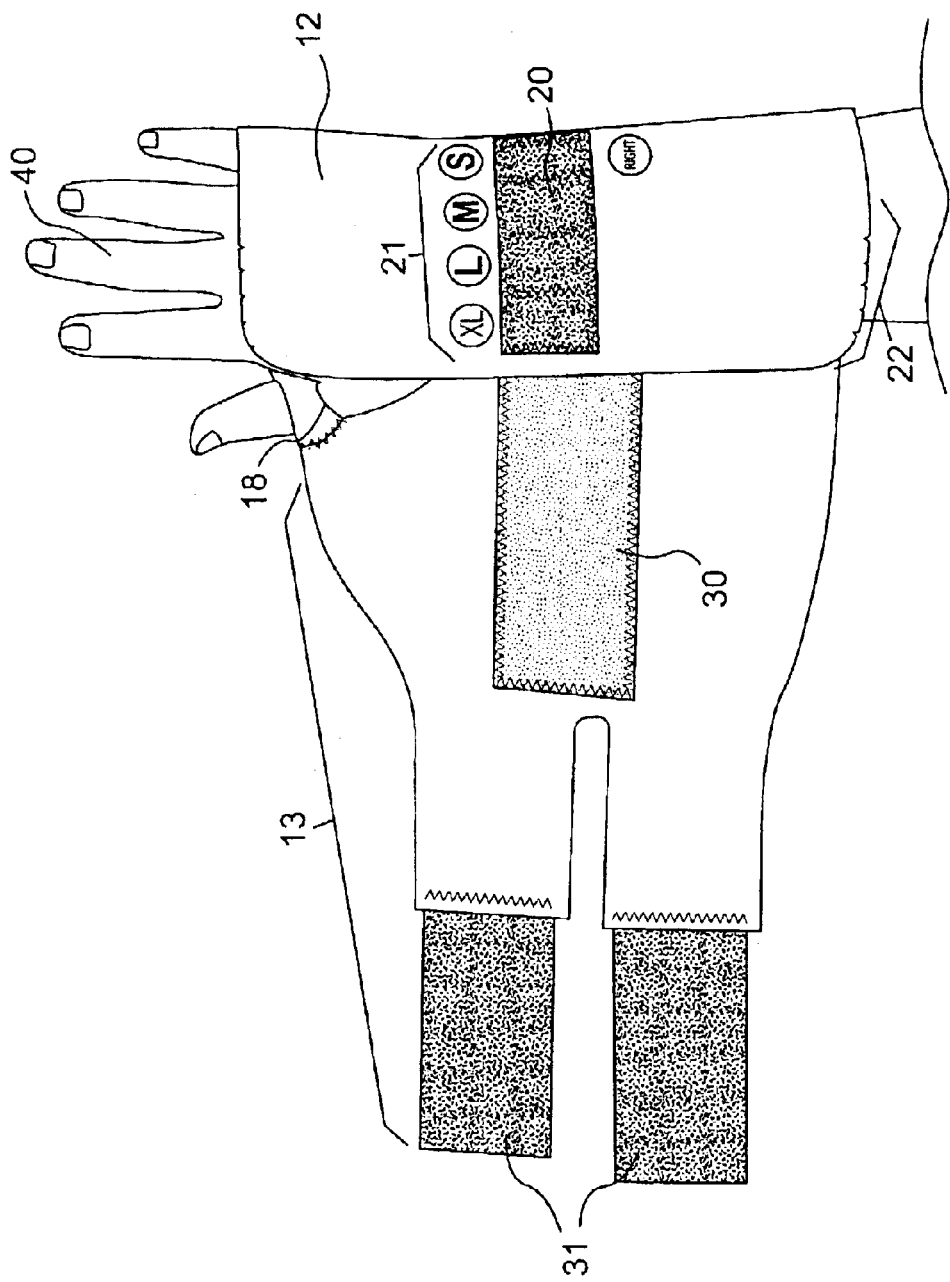

HAND AND WRIST BRACE AND KIT

The field of the invention is wrist and hand braces. Specifically, the invention relates to a brace adapted to be sized to any patient having virtually any size of hand and wrist.

BACKGROUND OF THE INVENTION

There exists presently a broad range of products available that act to immobilize or support the hand and a wrist of a patient in need. These products range from simple elastic bandages to complicated mechanical devices. Depending on the needs of a patient, an existing brace may provide palmar or dorsal support or both. Orthopedic specialists are able to diagnose and provide or prescribe appropriate braces in individual cases. Typically, a specialist has a substantial inventory of products to custom fit a patient regardless of the type of injury and the size of the patient. If not immediately available, then a specialist is often able to custom craft a device.

For general trauma clinics like a hospital emergency room, it can be burdensome to stock a large number of orthopedic braces. General clinics serve a broad range of medical needs for their patients. Braces such as flexible wraps come in different sizes for the needs of different sized patients. For instance, petite women are not the same size as large burly men. Presently, it is necessary to stock multiple sizes to keep a significant inventory available depending on a patient's needs. Also, braces can be very specialized as to what they treat. The result is that a potentially large inventory of braces is inevitable or a clinic runs the risk of having no brace available. In recent times of cost consciousness, all businesses including medical clinics are cutting back on their costs including their inventories. The result is a greater risk that necessary medical equipment might not be available.

SUMMARY OF THE INVENTION

Accordingly, it is an object of the present invention to solve the foregoing problems and to provide a hand and wrist brace and a kit that is adapted to be sized to different size patients. The kit provides variable support items that allow a medical professional to customize various components of the kit to meet the needs of a patient.

In one embodiment, the invention includes a brace for application around the wrist and hand of the patient. The brace includes a flexible sheet adapted to wrap around the wrist and hand of a patient. The sheet comprises a central palmar section, a first flap section connected to and disposed on one side of the palmar section, and a second flap section connected to and disposed on the opposite side of the palmar section from the first flap. Fasteners are attached to each of the first and second flap sections. Written indicia are printed onto one of the first or second flap sections, wherein the written indicia correspond to predetermined brace sizes. The brace may further include a palmar stay adapted to be removably attached to the central palmar section of the brace. The central palmar section may also comprise a integral pocket so that the palmar stay is insertable into that pocket. The fasteners may be hook and loop type fasteners. The written indicia may comprise a plurality of lines across the flap, whereby the lines may be used as a guide to trim unnecessary material from the sheet in accordance with the size of the wrist and hand of the patient. The flexible sheet may be comprised of an elastic material. The brace may further comprise a dorsal splint, the dorsal splint comprising a fastener, wherein the dorsal splint is adapted to fasten to at least one of the flap sections. The brace may also comprise a finger isolation splint, the finger isolation splint comprising a fastener, wherein the finger isolation splint is adapted to fasten to at least one of the flap sections.

In a still further alternative, a brace for application to the wrist and hand of a patient may comprise flexible sheet means for wrapping around the wrist and hand of a patient. The sheet means may comprise a central palmar section and flap means for wrapping around the wrist and hand, the wrap means connected to the palmar section. The brace further includes a fastener means for releasably securing the wrap means to itself after wrapping around the wrist and hand, the fastener means attached to the wrap means. The brace may further include written indicia printed onto the wrap means, wherein the written indicia correspond to predetermined brace sizes.

In a still further embodiment, the invention includes a kit for a brace for application around the wrist and hand of a patient. The kit comprises a brace, a finger isolation splint, and a dorsal splint. The brace comprises a flexible sheet adapted to wrap around the wrist and hand of a patient. The sheet comprises a central palmar section, a first flap section connected to and disposed on one side of the palmar section, and a second flap section connected to and disposed on the opposite side of the palmar section from the first flap. The brace further includes fasteners attached to each of the first and second flap sections and written indicia printed onto one of the first or second flap sections. The written indicia correspond to predetermined brace sizes. The finger isolation splint comprises a fastener, wherein the finger isolation splint is adapted to fasten to at least one of the flap sections. The dorsal splint comprises a fastener, wherein the dorsal splint is adapted to fasten to at least one of the flap sections.

BRIEF DESCRIPTION OF THE DRAWINGS

FIGS. 2A–2C demonstrate how a brace like the brace shown in FIG. 1 is worn by a patient.

DETAILED DESCRIPTION OF THE PREFERRED EMBODIMENTS

Figure 1A:
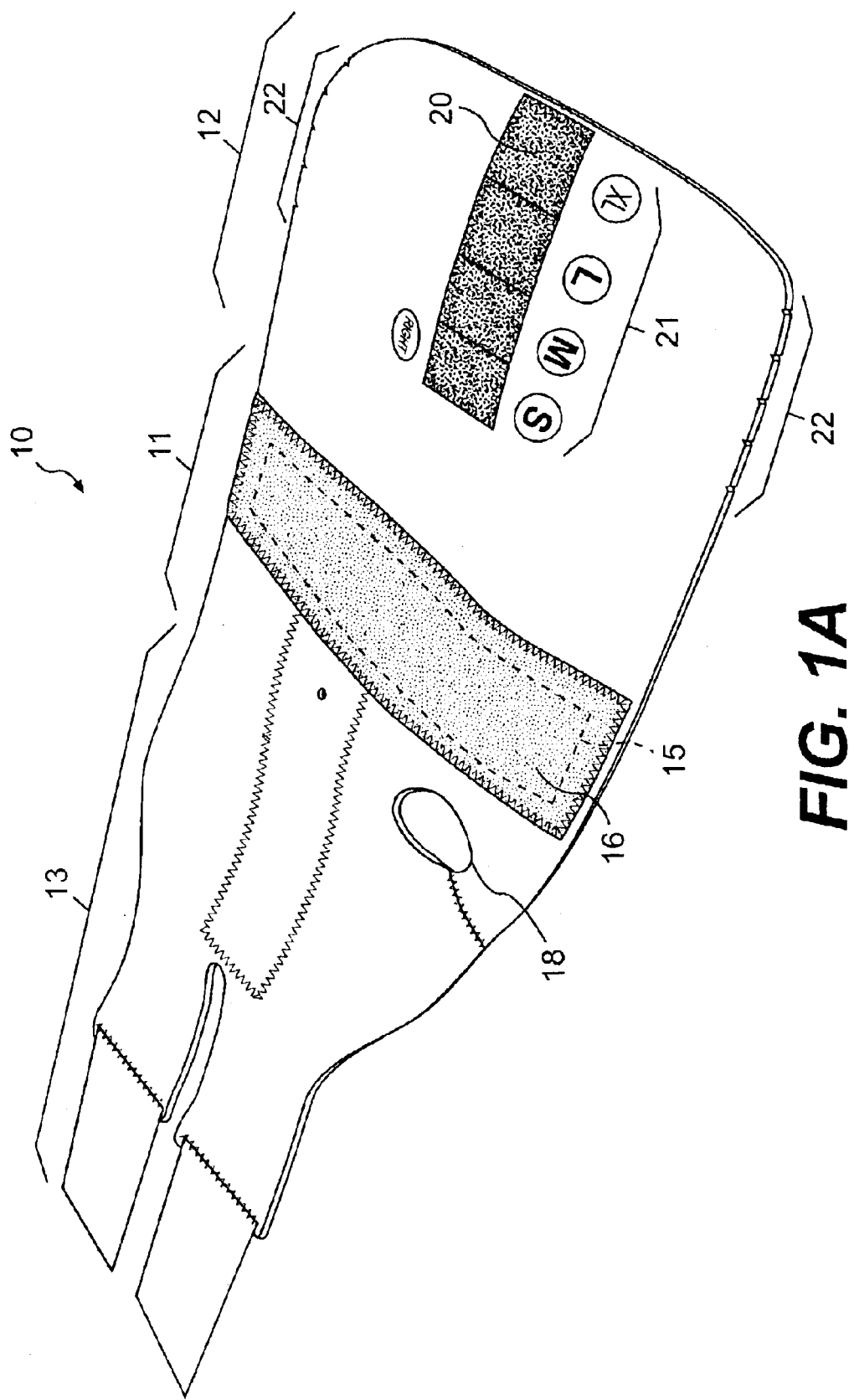
FIGS. 1A and 1B are top perspective and bottom perspective views respectively of one embodiment of a brace in accordance of the present invention.
Figure 1B:
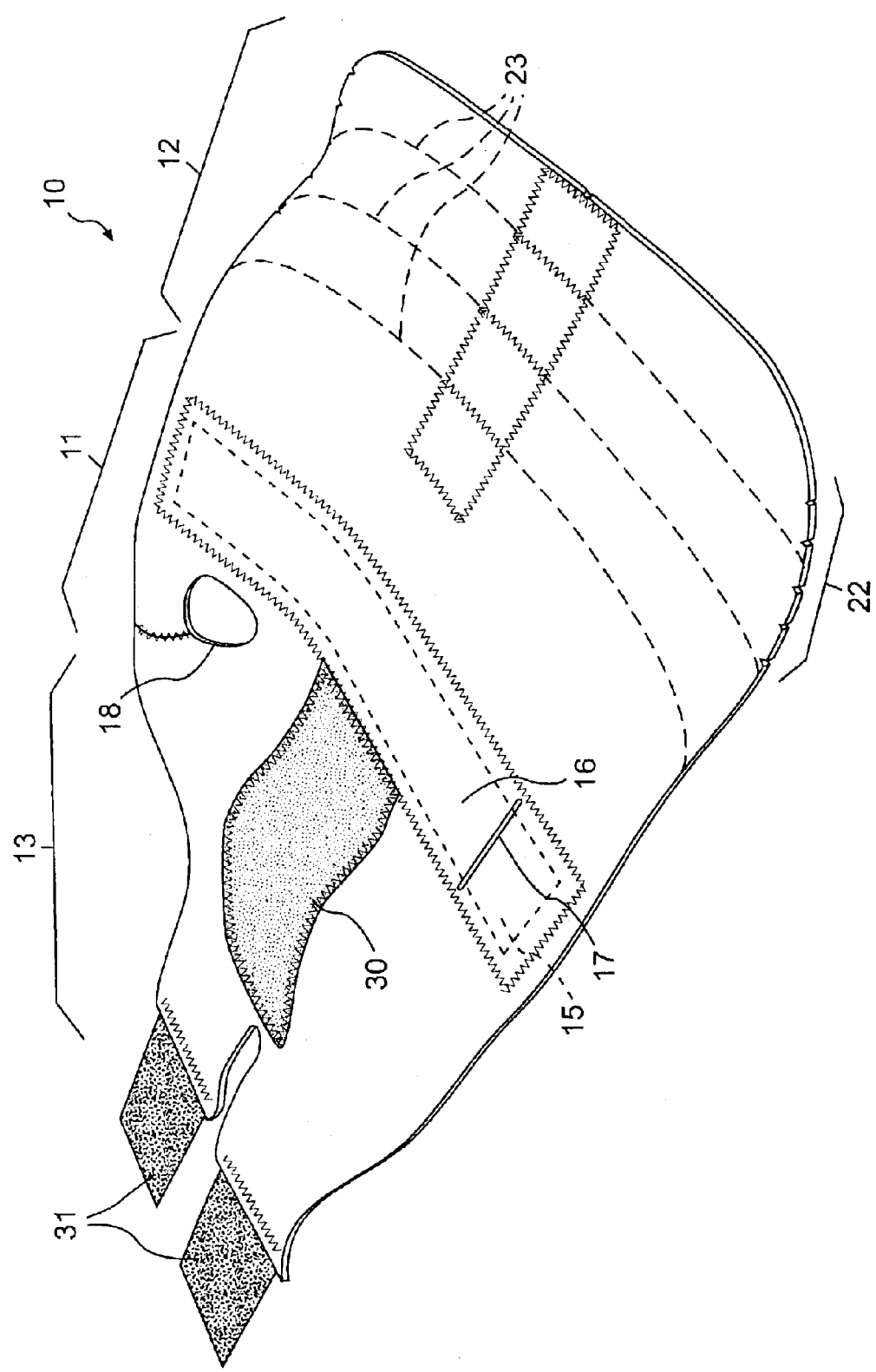

FIGS. 1A and 1B illustrate the top and bottom respectively of one embodiment of a wrist and hand brace 10 in accordance with the present invention. The brace 10 is a flexible sheet of material adapted to wrap around the wrist and hand of a patient in order to provide support and/or immobilization. The actual material that makes up the body of the brace 10 is preferably flexible and stretchable. It may be a laminate and have an outside layer that is both comfortable on the skin and that has a nap or other weave or material that is receptive to hook fasteners in a hook and loop fastening arrangement. In a preferred embodiment, the brace is made up from a sheet of $\frac{1}{16}$ inch neoprene with a tan UBL/Black nylon fabric layer.

The brace 10 is made up of a central palmar section 11 and two flap sections 12 and 13. The palmar section 11 is adapted to generally align with the palm and inside wrist of a patient. The palmar section 11 includes an integral pocket 15 that is stitched onto the brace 10. The pocket 15 includes an aperture 17 into which may be inserted a palmar stay 16. The stay 16 is preferably made from a rigid but conformable metal material such as aluminum so that it may be bent by a caregiver to conform to the individual shape of a patient's wrist and palm. The palmar section 11 also includes a thumb hole 18 adapted to receive the thumb of patient when the brace is wrapped around the wrist and hand of a patient.

The first flap section 12 is attached on one side of the palmar section 11. They may all be one actual piece of material, or the palmar and flap sections 11, 12 and 13 may all be separate and separately attached to each other. The first flap 12 includes a patch of hook and loop fastener 20. This patch 20 is stitched onto the first flap section 12 in approximately the center of that section. Alternatively, whether or not the fastener is a hook and loop type, the fastener may be attached at other locations around a flap section. The first flap section further includes the written indicia 21 that correspond to various predetermined sizes for the brace 10. In other words, the written indicia 21 correspond to small, medium, large and extra large. In this way, a care giver fitting the brace on a patient with a petite wrist and hand may trim off a portion of the first flap section 12 in order to more easily wrap around that patient's wrist and hand. Conversely, a large person having a large wrist and hand will require the entire brace without trimming in order to comfortably and favorably wrap a wrist and hand. Indentations 22 in the first flap section 12 are meant to guide a health care provider in trimming off portions of the flap section when fitting the brace 10 to a wrist and hand. In addition to the written indicia 21 and indentations 22 shown, lines 23 or perforations or other indicia may be placed on a brace in order to provide a very specific guide for trimming by a health care provider when fitting a brace 10. Still further, the written indicia 21 shown in the figures may easily be replaced with a numeric system or other predetermined size indicator to assist in the sizing of a brace. Additional size indicia such as extra small (XS) and extra extra large (XXL) may allow a broader range of sizes.

Second flap section 13 is attached to the side of palmar section 11 on the opposite side from the first flap section 12. The second flap section 13 includes a patch 30 of loops or hooks that act as a fastener when the brace is wrapped around onto itself. Additional fasteners 31 are patches of hooks or loops adapted to secure the end of the second flap section 13 onto the face of the brace 10 when it is wrapped around itself.

Figure 2A:
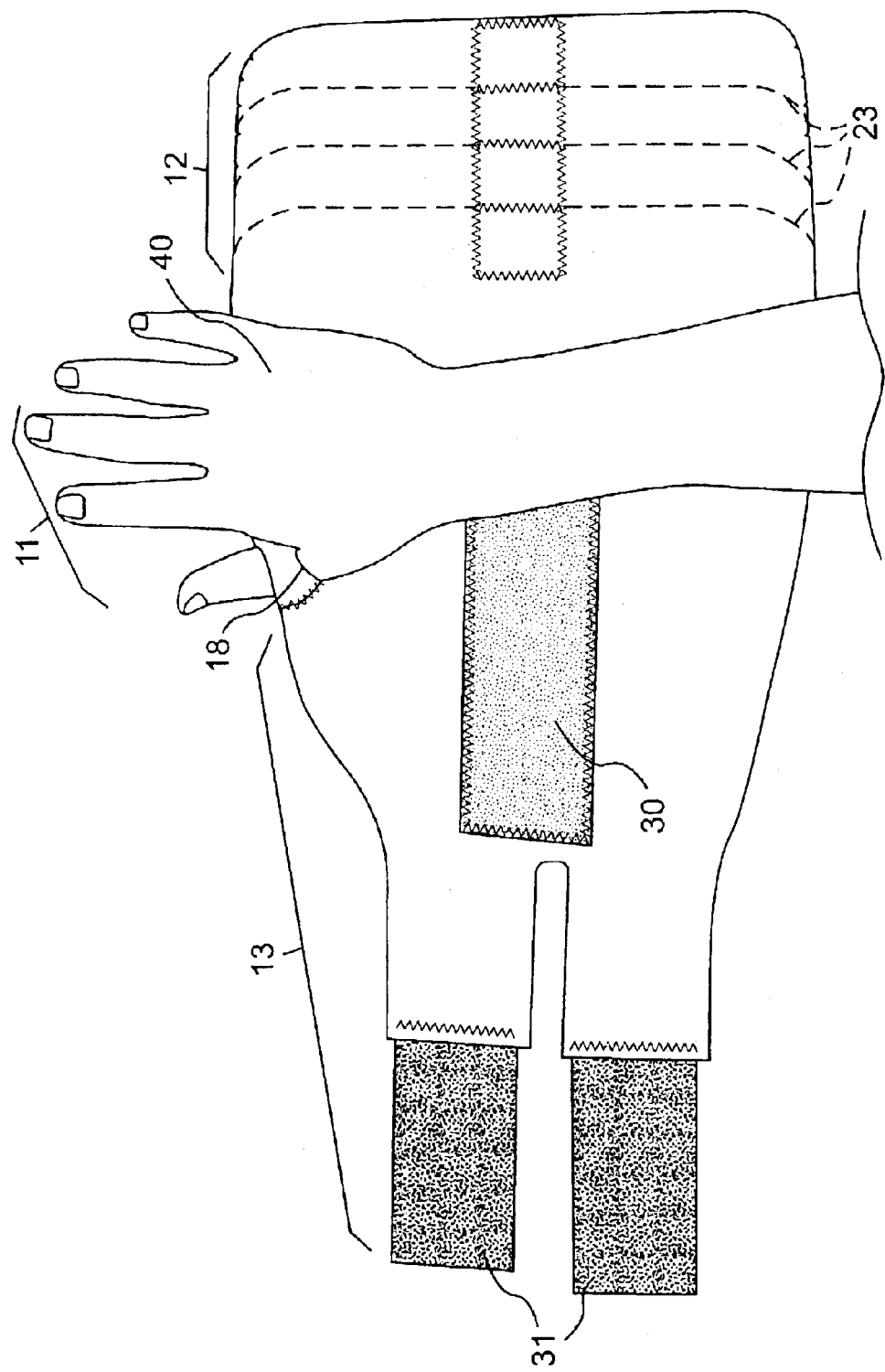
Figure 2C:
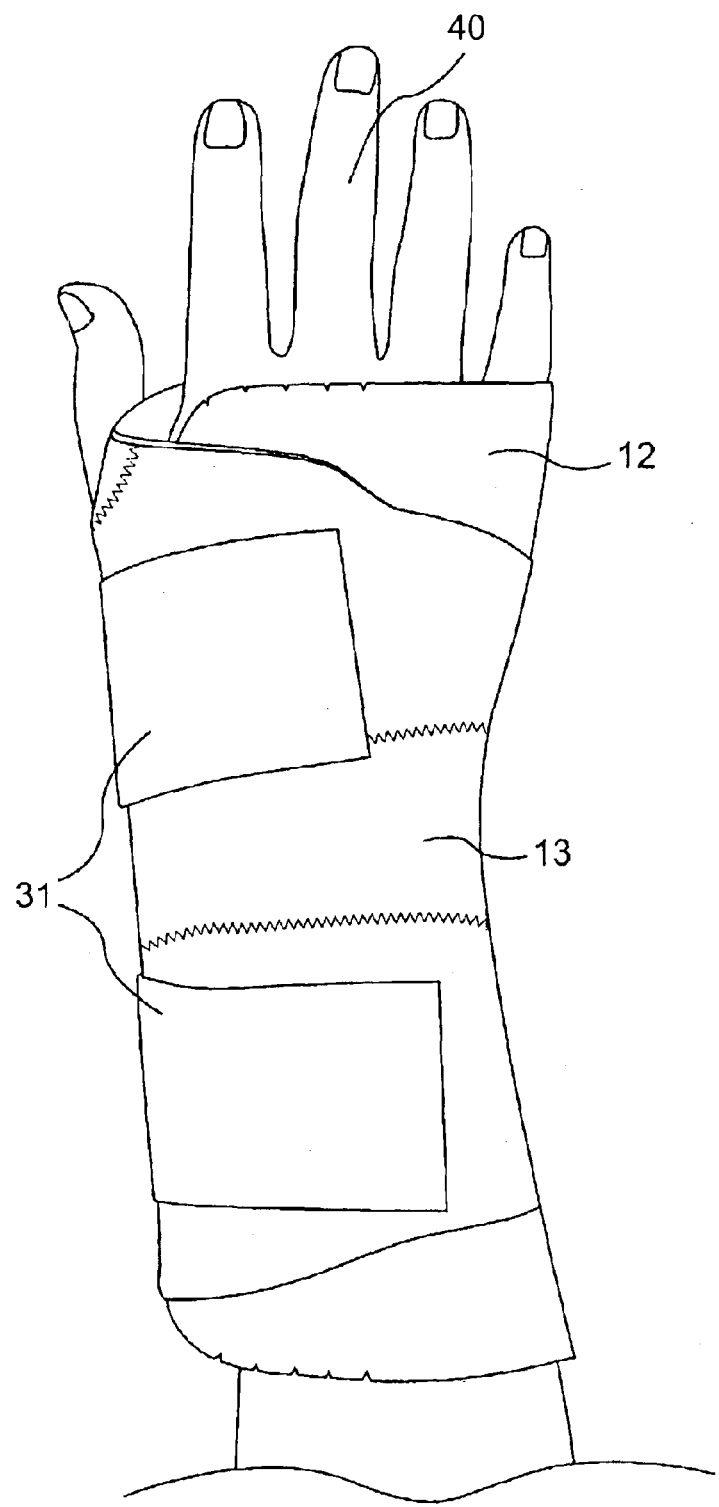

FIGS. 2A through 2C demonstrate the actual method in which the brace 10 is applied to a person's hand and wrist 40. A person merely inserts their thumb through the thumb hole 18. (All of the figures herein illustrate a brace for a right hand and wrist. Of course a corresponding brace may be designed for a left hand and wrist.) The first flap section 12 is then wrapped around the wrist in one direction. That flap section is then trimmed to an appropriate size for that patient. The flap section 12 in FIG. 2B is shown without any portion of that section trimmed off. The second flap section 13 is then wrapped around the hand and wrist 40 in the opposite direction from the first flap section 12. In this way, the patches 20 and 30 are engaged and fastened to each other. Similarly, the fasteners 31 are attached to the flap section 13 that is wrapped around itself.

Figure 3A:
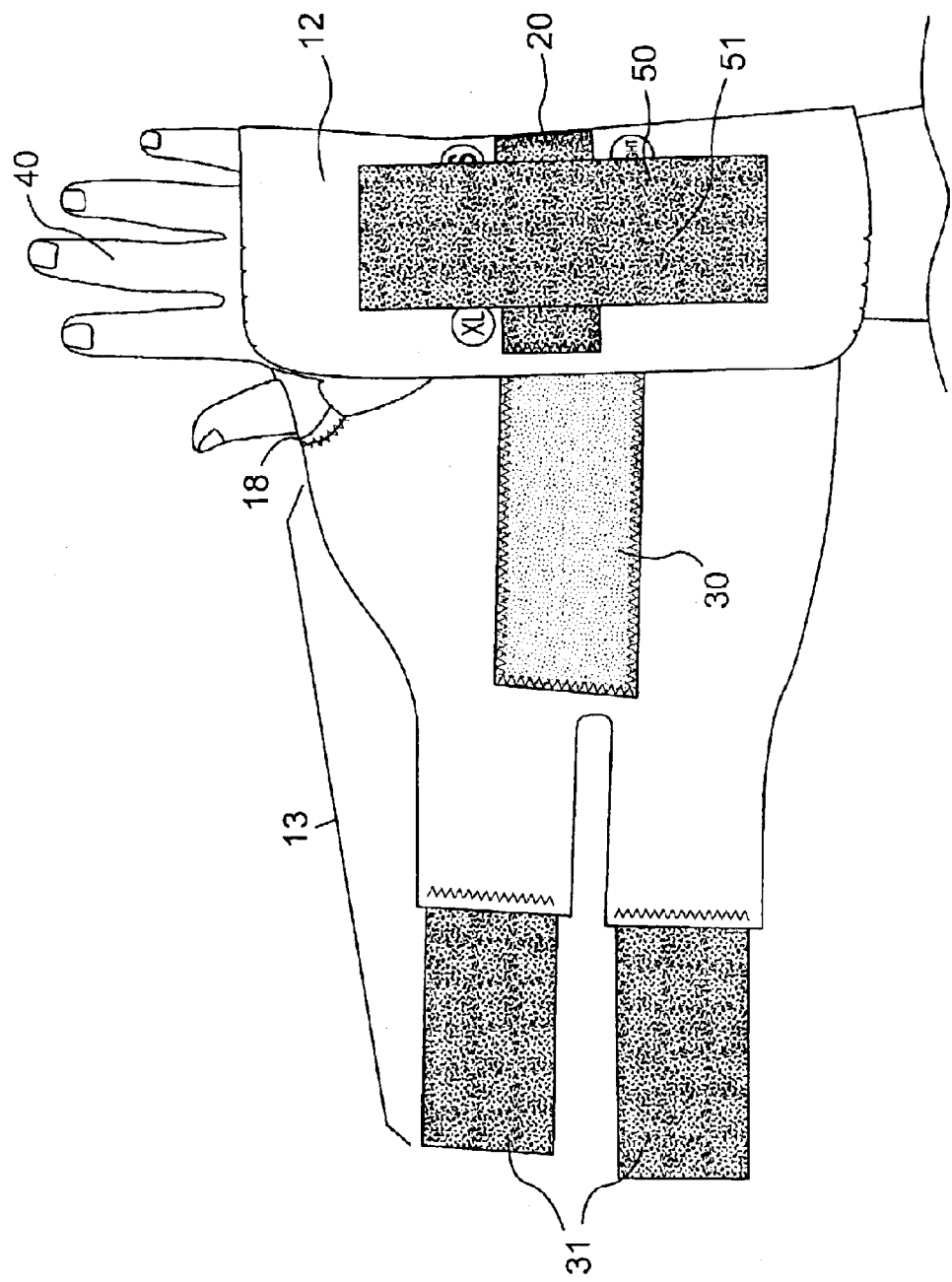
FIGS. 3A and 3B demonstrate how a dorsal splint is applied and incorporated in a brace illustrated in FIGS. 1A and 1B.
Figure 3B:
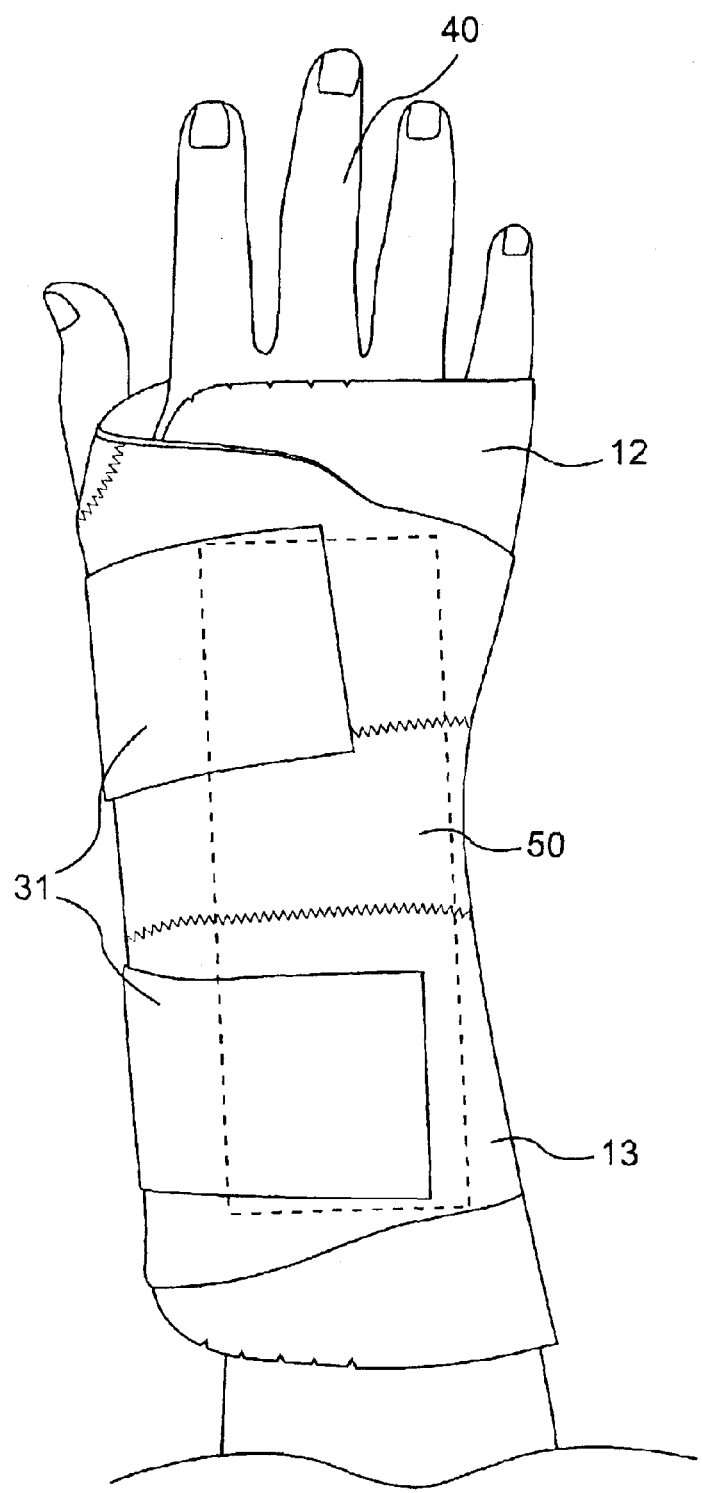

FIGS. 3A and 3B further demonstrate the use of the brace 10 in connection with a dorsal splint 50. The dorsal splint 50 as shown is encased in a fastener patch 51. The splint 50 is preferably made of a rigid metallic material that is able to be conformed by a health care giver to the appropriate shape to support or immobilize the wrist and hand of a particular patient. The patch 51 of hook and loop fastener allows the dorsal splint 50 to be engaged and secured to the brace 10 as it is wrapped around the wrist and hand of a patient as shown in FIGS. 3A and 3B.

Figure 4A:
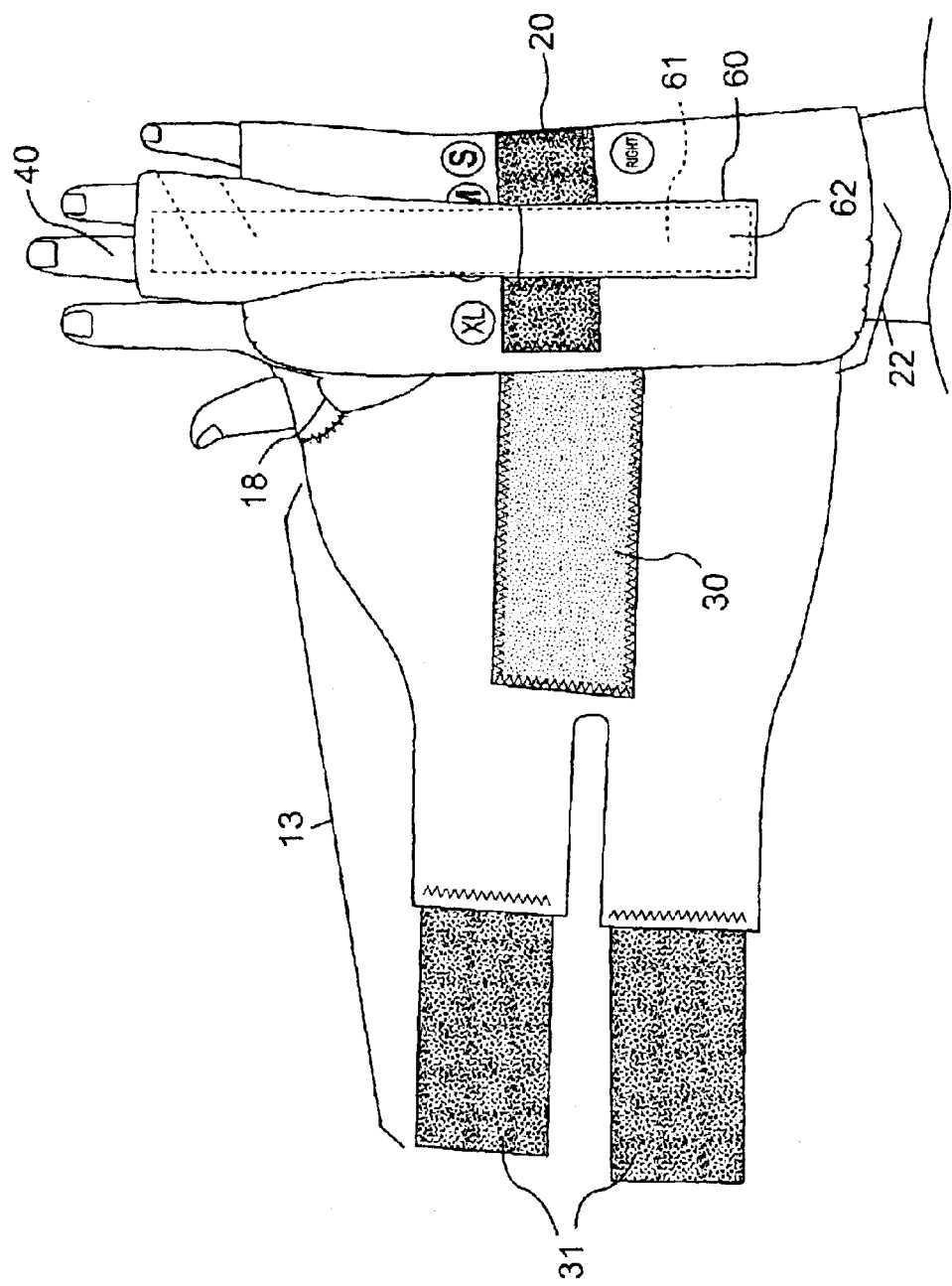
FIGS. 4A and 4B illustrate a finger isolation splint and how it is incorporated into the brace illustrated in FIGS. 1A and 1B.
Figure 4B:
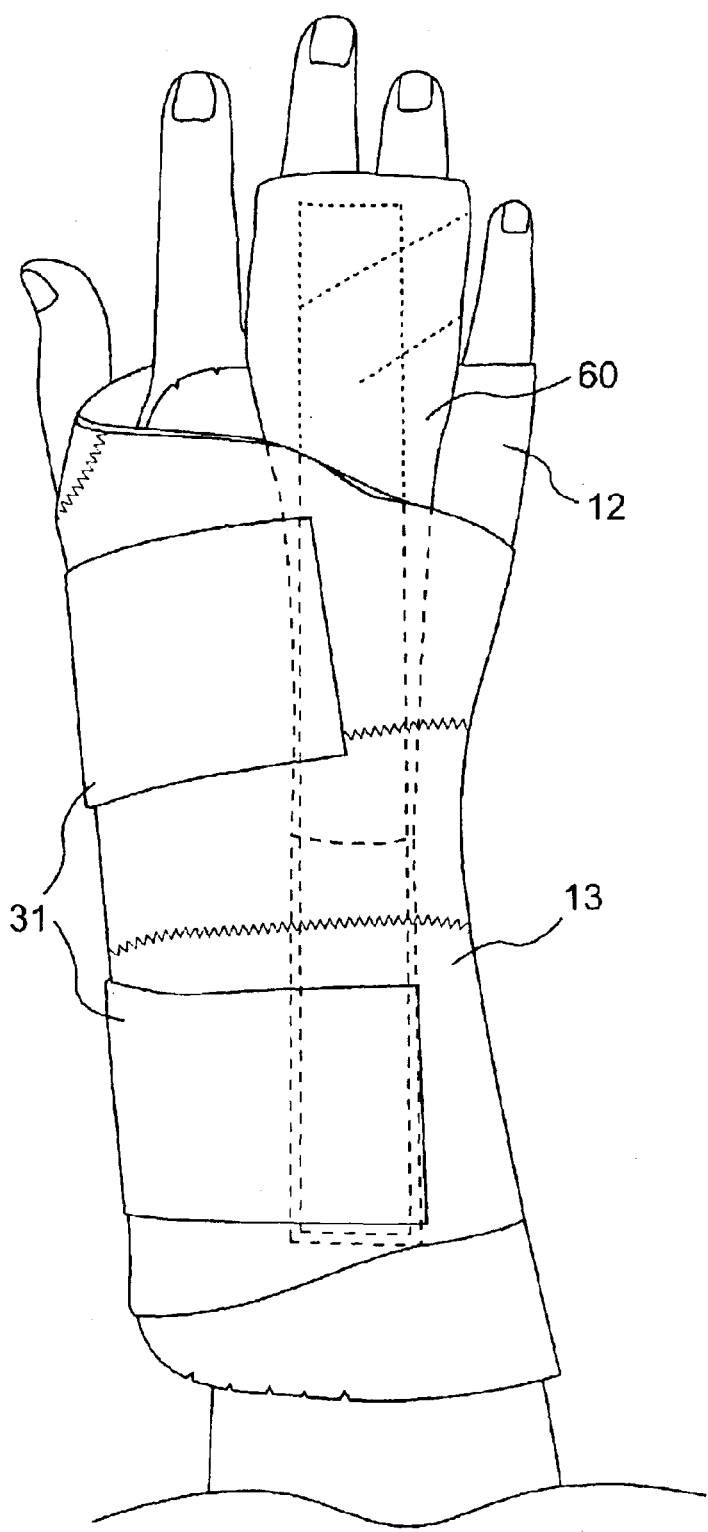

FIGS. 4A and 4B demonstrate a still further embodiment of the invention in which a finger splint 60 is incorporated with the brace 10. The splint 60 includes a rigid metal piece 61 and a fastener material 62 that is wrapped around it. The splint section 61 is made of a rigid metallic material that is able to be conformed by a health care giver. The fastener material 62 allows the splint 60 to be wrapped up within the brace 10 as demonstrated in FIGS. 4A and 4B.

Other types of finger and thumb support devices can be used consistent with the brace described herein. Similarly, other attachments like a gel spot may be secured in and/or under the brace to provide some other types of relief.

It is envisioned that the brace, dorsal stay, finger splint and any other support or therapeutic component could be sold together as a kit. In this way, the single kit could be maintained in inventory by a medical facility and be used for a broad range of immobilization and support purposes for a broad range of sizes depending on a patient. Another alternative stocking method is to maintain an inventory of the components individually so that they would only be used as needed.

The fasteners discussed herein are all been based on the hook and loop fastener type of technology. In addition to this technology, other fasteners might include snaps, pins, or other hook and claw arrangements.

Additionally, although the combinations of finger splint and brace and dorsal splint and brace have been discussed herein, it is envisioned that two or more braces and/or splints may be used and incorporated for a given application depending on the needs of a patient. For example, a thumb splint as well as a ring finger splint could be separately wrapped up and secured in a brace to give support to those appendages.

While the invention has been described with reference to specific embodiments thereof, it will be understood that numerous variations, modifications and additional embodiments are possible, and all such variations, modifications, and embodiments are to be regarded as being within the spirit and scope of the invention.

What is claimed is:

1. A brace for application around the wrist and hand of a patient, the brace comprising:
   (a) a flexible sheet adapted to wrap around the wrist and hand of a patient, the sheet comprising:
      a central palmar section,
      a first flap section connected to and disposed on one side of the palmar section,
   and
      a second flap section connected to and disposed on the opposite side of the palmar section from the first flap;
   (b) fasteners to each of the first and second flap sections; and
   (c) written indicia printed onto one of the first or second flap sections, wherein the written indicia correspond to predetermined brace sizes, and further wherein the written indicia comprises a plurality of lines across the flap, whereby the lines are used as a guide to trim unnecessary material from the sheet in accordance with the size of the wrist and hand of the patient;

whereby the brace is adapted to be wrapped around and support the wrist and hand of a patient.

2. A brace as described in claim 1, further comprising a palmar stay adapted to be removably attached to to the central palmar section of the brace.

3. A brace as described in claim 2, wherein the central palmar section further comprises an integral pocket, and the palmar stay is insertable into the integral pocket.

4. A brace as described in claim 1, wherein the fasteners are hook and loop type fasteners.

5. A brace as described in claim 1, wherein the flexible sheet is comprised of an elastic material.

6. A brace for application to the wrist and hand of a patient, the brace comprising:
(a) a flexible sheet for wrapping around the wrist and hand of a patient, the sheet comprising
a central palmar section, and
means for wrapping around the wrist and hand, the means for wrapping connected to the palmar section,
(b) a fastener means for releasably securing the means for wrapping to itself after wrapping around the wrist and hand, the fastener means attached to the means for wrapping; and
(c) written indicia printed onto the means for wrapping, wherein the written indicia correspond to predetermined brace sizes, and further wherein the written indicia comprises a plurality of lines across the means for wrapping, whereby the lines are used as a guide to trim unnecessary material from the sheet in accordance with the size of the wrist and hand of the patient;
whereby the brace is adapted to be wrapped around and support the wrist and hand of a patient.

7. A brace as described in claim 6, further comprising a palmar stay adapted to be removably attached to the central palmar section of the brace.

8. A brace as described in claim 7, wherein the central palmar section further comprises an integral pocket, and the palmar stay is insertable into the integral pocket.

9. A brace as described in claim 6, wherein the fastener means is a hook and loop type fastener.

10. A brace as described in claim 6, wherein the sheet is comprised of an elastic material.

11. A kit for a brace for application around the wrist and hand of a patient, the kit comprising:
a brace comprising:
(a) a flexible sheet adapted to wrap around the wrist and hand of a patient, the sheet comprising:
a central palmar section,
a first flap section connected to and disposed on one side of the palmar section, and
a second flap section connected to and disposed on the opposite side of the palmar section from the first flap;
(b) fasteners attached to each of the first and second flap sections;
(c) written indicia printed onto one of the first or second flap sections; wherein the written indicia correspond to predetermined brace sizes, and further wherein the written indicia comprises a plurality of lines across the flap, whereby the lines are used as a guide to trim unnecessary material from the sheet in accordance with the size of the wrist and hand of the patient;
a finger isolation splint comprising a fastener, wherein the finger isolation splint is adapted to fasten to at least one of the flap sections; and
a dorsal splint comprising a fastener, wherein the dorsal splint is adapted to fasten to at least one of the flap sections.

* * * * *